(12) United States Patent
Weitzman et al.

(10) Patent No.: US 12,171,440 B2
(45) Date of Patent: Dec. 24, 2024

(54) SURGICAL INSTRUMENT WITH BENDED SHAFT

(71) Applicant: CAREVATURE MEDICAL LTD., Rehovot (IL)

(72) Inventors: Yoseph Weitzman, Tel Aviv (IL); Eran Miller, Moshav Beit Elazari (IL); Ely Ashkenazi, Jerusalem (IL); David Skorohod, Netanya (IL)

(73) Assignee: CAREVATURE MEDICAL LTD., Rehovot (IL)

( * ) Notice: Subject to any disclaimer, the term of this patent is extended or adjusted under 35 U.S.C. 154(b) by 238 days.

(21) Appl. No.: 17/866,919

(22) Filed: Jul. 18, 2022

(65) Prior Publication Data
US 2023/0046328 A1 Feb. 16, 2023

Related U.S. Application Data

(63) Continuation of application No. 16/476,424, filed as application No. PCT/IL2018/050046 on Jan. 11, 2018, now Pat. No. 11,419,614.
(Continued)

(51) Int. Cl.
*A61B 17/16* (2006.01)
*A61B 17/32* (2006.01)
(Continued)

(52) U.S. Cl.
CPC .... *A61B 17/1631* (2013.01); *A61B 17/32002* (2013.01); *A61B 2017/00738* (2013.01); *A61B 2034/2072* (2016.02)

(58) Field of Classification Search
CPC .................. A61B 17/1631; A61B 2017/00738
See application file for complete search history.

(56) References Cited

U.S. PATENT DOCUMENTS 1,678,335 A * 7/1928 Gaston .................... F16C 1/262
464/57
4,811,735 A 3/1989 Nash et al.
(Continued)

FOREIGN PATENT DOCUMENTS

DE 202008011612 11/2008
DE 102009021135 11/2010
(Continued)

OTHER PUBLICATIONS

PCT International Search Report for International Application No. PCT/IL2018/050046, mailed Apr. 17, 2018, 9pp.
(Continued)

*Primary Examiner* — Andrew Yang
(74) *Attorney, Agent, or Firm* — The Roy Gross Law Firm, LLC; Roy Gross

(57) ABSTRACT

A surgical bone cutting device, including a handle configured to facilitate operation and control of said device by an operator, and an elongated hollow member extending from the handle, the hollow member having a proximal end and a distal end; wherein the hollow member includes an opening at the distal end thereof and a rotatable cutting element extending through the opening, and wherein the hollow member includes a first bend at the proximal end thereof, such that the part of the hollow member distal to the proximal bend is offset a central axis of the hand.

12 Claims, 8 Drawing Sheets

Related U.S. Application Data

(60) Provisional application No. 62/445,051, filed on Jan. 11, 2017.

(51) Int. Cl.
    *A61B 17/00*    (2006.01)
    *A61B 34/20*    (2016.01)

(56) References Cited

U.S. PATENT DOCUMENTS

| | | |
|---|---|---|
| 5,286,253 A | 2/1994 | Fucci |
| 5,593,416 A | 1/1997 | Donahue |
| 5,851,208 A | 12/1998 | Trott |
| 5,922,003 A | 7/1999 | Anctil et al. |
| 6,053,922 A | 4/2000 | Krause et al. |
| 7,147,650 B2 | 12/2006 | Lee |
| 7,879,037 B2 | 2/2011 | Brunnett et al. |
| 10,610,215 B2 | 4/2020 | Anderson et al. |
| 2005/0090849 A1 | 4/2005 | Adams |
| 2011/0286098 A1* | 11/2011 | Hauri ............... A61B 34/20 |
| | | 359/543 |
| 2012/0152045 A1 | 6/2012 | Isobe et al. |
| 2015/0230791 A1 | 8/2015 | Smith et al. |
| 2016/0074046 A1 | 3/2016 | Sennett et al. |
| 2018/0028266 A1* | 2/2018 | Barnes ............... A61B 17/1695 |

FOREIGN PATENT DOCUMENTS

| | | |
|---|---|---|
| EP | 2434965 A1 | 4/2015 |
| JP | 2007-503921 | 3/2007 |
| JP | 2013-144203 A | 7/2013 |
| JP | 2015-221476 A | 12/2015 |
| WO | 2005020827 | 3/2005 |

OTHER PUBLICATIONS

PCT Written Opinion for International Application No. PCT/IL2018/050046, mailed Apr. 17, 2018, 7pp.

* cited by examiner

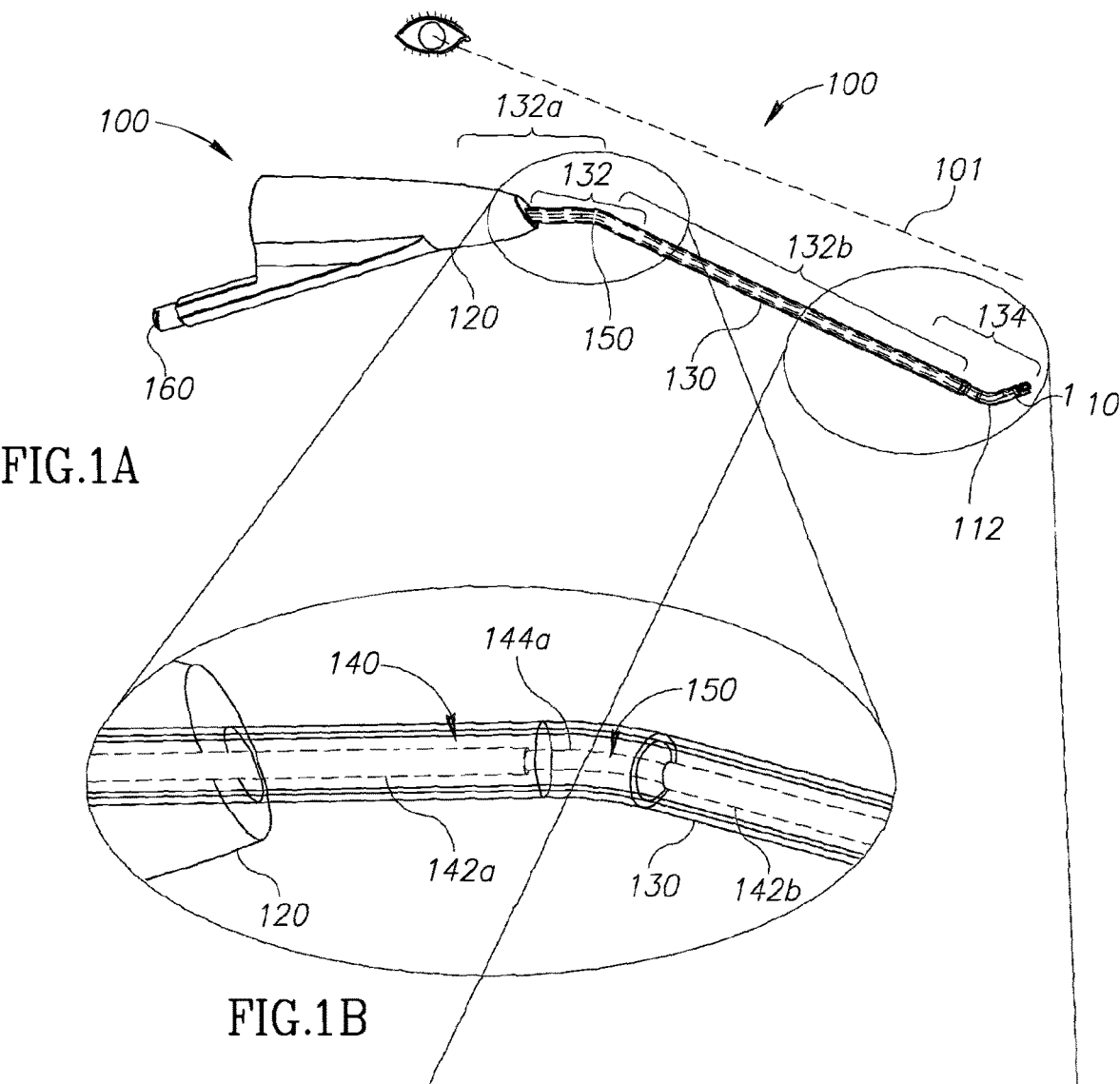
FIG.1A
FIG.1B
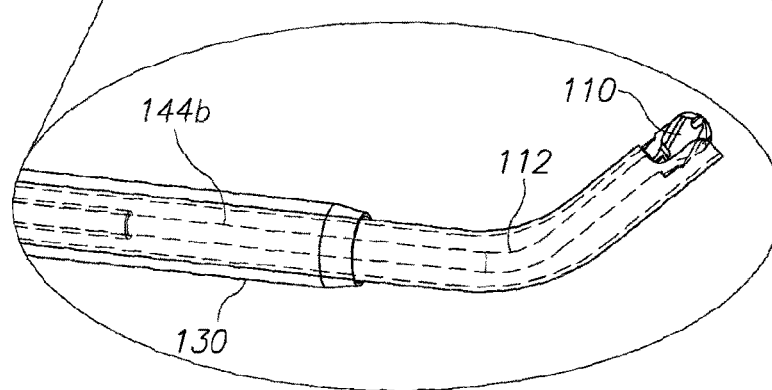
FIG.1C

SURGICAL INSTRUMENT WITH BENDED SHAFT

CROSS REFERENCE TO RELATED APPLICATIONS

This application is a continuation of U.S. patent application Ser. No. 16/476,424 filed on Jul. 8, 2019, which is a National Phase of PCT Patent Application No. PCT/IL2018/050046 having International filing date of Jan. 11, 2018, which claims the benefit of priority of U.S. Provisional Application No. 62/445,051 filed on Jan. 11, 2017. The contents of the above applications are all incorporated by reference as if fully set forth herein in their entirety.

TECHNICAL FIELD

The present disclosure generally relates to the field of surgical tools for removal of tissue, preferably bone tissue.

BACKGROUND

Excess body tissue can lead to pathological conditions and pain, especially when the excess tissue affects the nervous system. One common problem is Spinal Stenosis, Degenerative Disc Disease and other spine pathologies where excess bone tissue affects the spinal cord and related neural elements. Two of the most prominent conditions associated with narrowing (stenosis) of the spinal or nerve root canal are: excess bone growth into the spinal or nerve root canal resulting in a neurological deficit, and bulging or herniated disc.

Spinal Stenosis and Degenerative Disc Disease is typically treated by removing all or part of the vertebral body or bone spurs pushing into the neural elements, usually as a way to decompress the spinal nerves to alleviate or treat the neurological deficit. As to a herniated disc, it is commonly treated with a surgical procedure called discectomy, during which herniated disc material that presses against the nerve root or spinal cord is removed.

The tissue intended for removal is often hard tissue, such as bone, which requires special physical properties from the cutting or grinding member. Moreover, the undesired tissue is typically located in positions that are difficult to reach and the surgical procedures require selective removal of tissue while avoiding causing harm to surrounding tissue, e.g. dural sack and/or dural nerves that can be fragile or vulnerable to damage.

There is thus a need in the art for surgical instruments that provide selective cutting/resection/removal of hard-to-access tissue, while mitigating the harm of damaging surrounding tissue.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other advantages or improvements.

According to some embodiments, there is provided a surgical device including a handle configured to facilitate operation and control of the device by an operator, an elongated hollow member extending from the handle, the hollow member having a proximal end and a distal end; wherein the distal end of the hollow member includes an opening, a torque transferring element/assembly, configured to be placed within the elongated hollow member, and a rotatable cutting element attached to said torque transferring element/assembly and extending through or positioned at the opening; wherein the proximal end of the hollow member includes at least one proximal bend configured to ensure that the part of the hollow member, which is distal to the proximal bend, is offset a central axis of the handle, wherein said torque transferring element/assembly is configured to affect rotary motion of the rotatable cutting element.

According to some embodiments, the torque transferring element/assembly is configured to facilitate rotational speed of at least 15,000 RPM, at least 20,000 RPM, at least 30,000 RPM, at least 40,000 RPM, or at least 50,000 RPM and a torque of at least 4 Ncm, while being bent and/or kept in a bent configuration. According to some embodiments, the torque transferring element/assembly is configured to facilitate a bidirectional rotational speed of at least 15,000 RPM, at least 20,000 RPM, at least 30,000 RPM, at least 40,000 RPM, or at least 50,000 RPM and a torque of at least 4 Ncm.

In surgical procedures for removal of excess tissue, it is of high importance to perform selective removal only of the undesired tissue, while mitigating any removal or damage of surrounding tissue.

Advantageously, the offset configuration of the shaft relative to the handle, caused by the proximal bend, is configured to ensure that the distal end of the shaft, carrying the cutter, is not concealed by the surgeon's hand, by the handle, by the tube through which it is delivered, such as, but not limited to, an endoscope, and/or when utilizing surgical microscopes. Better visualization of the work area is thus assured.

According to some embodiments, the shaft may include an additional proximal bend. Such double bending allows obtaining a configuration in which part of the hollow member downstream the proximal bends is substantially parallel to the central axis of the handle.

Additionally or alternatively, the device may include one or more medial bends positioned between the proximal and distal ends of the hollow elongated member, such as, but not limited to, around halfway the length of the hollow elongated member. Advantageously, such medial bends may ensure an unhindered line of site when utilizing the device in robotic/robot assisted surgeries.

As a further advantage, the torque transferring element/assembly may include one or more support structures configured to prevent helixing of the torque transferring element/assembly. This is of particular importance due to need for torque delivery over bent configurations and at high rotational speed.

An existing solution for torque delivery utilizes a long and hard stainless-steel wire (1-1.5 mm diameter) that, while allowing bending of the shaft (hollow elongated member), at high speed (60K RPM) and torque requires a large bending radius, typically more than 100 mm, which is too big for the human anatomy.

Another solution for torque delivery applies a torque element made of numerous strips made by cutting (e.g. by cutting a tube made of three layers with various direction (counter clockwise and clockwise) intermittently, with a fitted guide. Such a solution, while allowing a bending radius of 30-40 mm, cannot be operated at high-speed, such as above to 12K RPM.

Furthermore, both solutions incur high friction between the rotatable torque transferring element and the guiding shaft, which friction often causes overheating and mechanical failure of the torque transferring element.

According to some embodiments, a shaft with a single proximal bend may be of particular advantage when utilizing surgical microscopes and/or endoscopes that have short focal length, and that preferably would be located parallel to the shaft and close to the surgical site, this, since the handle is prevented from interfering with the illumination path and the line of sight of the endoscope.

According to some embodiments, a shaft with two proximal bends may be advantageous for maintaining line of sight in particular for open surgeries and/or endoscopic procedures.

According to some embodiments, the hollow member may further include a distal bend configured to allow access to difficult to reach target tissue/hidden anatomies, such as, but not limited to, between adjacent vertebrae and/or sites within/near the spinal canal.

That is, whereas the distal bend is configured to enable access and maneuverability of the device at hidden anatomies, e.g. between or underneath vertebral discs, the proximal bend(s) is/are configured to enable an unhindered line of site of the device's distal tip, regardless of it having a distal bend or not.

According to some embodiments, there is provided a surgical device, including a handle configured to facilitate operation and control of the device by an operator, an elongated hollow member extending from the handle, the hollow member having a proximal end and a distal end, wherein the distal end of the hollow member includes an opening, a torque transferring element/assembly, configured to be placed within the elongated hollow member, and a rotatable cutting element attached to said torque transferring element/assembly and extending through or positioned at the opening; wherein the proximal end of the hollow member includes at least one proximal bend configured to ensure that the part of the hollow member, which is distal to the proximal bend, is offset a central axis of the handle, wherein said torque transferring element/assembly is configured to affect rotary motion of the rotatable cutting element.

According to some embodiments, the torque transferring element/assembly is configured to facilitate (optionally bi-directional) rotational speed of at least 40,000 RPM and a torque of at least 4 Ncm.

According to some embodiments, the bend enables the operator to maintain visibility of the cutting tip when holding the handle and or when utilizing endoscopes or surgical microscopes.

According to some embodiments, the first proximal bend comprises a bending angle of up to 90 degrees relative to the central axis of the handle. According to some embodiments, the first proximal bend comprises a bending angle of 20-60 degrees relative to the central axis of the handle. According to some embodiments, the first proximal bend comprises a bending radius of less than 20 mm.

According to some embodiments, the device further comprises a second proximal bend. According to some embodiments, wherein part of the hollow member distal to the first and second proximal bends is substantially parallel to the central axis of the handle, as used herein, the term "substantially" may refer to +/−10 degrees or +/−5 relative to the central axis of the handle.

According to some embodiments, the second proximal bend comprises a bending angle of up to 90 degrees relative to the central axis of the handle. According to some embodiments, the second proximal bend comprises a bending angle of 20-60 degrees relative to the central axis of the handle.

According to some embodiments, the second proximal bend comprises a bending radius of less than 20 mm.

According to some embodiments, the device further includes a bend at a distal end thereof. According to some embodiments, the distance between the distal bend and the opening is less than 20 mm.

According to some embodiments, the distal bend comprises a bending angle of up to 90 degrees relative to part of the hollow member distal to the first or second proximal bend. According to some embodiments, the distal bend comprises a bending angle of 0-60 degrees relative to part of the hollow member distal to the first or second proximal bend. According to some embodiments, the distal bend comprises a bending radius of less than 10 mm relative to part of the hollow member distal to the first or second proximal bend.

According to some embodiments, the distal end is offset to the central axis of the handle. According to some embodiments, the distal end is parallel to the central axis of the handle.

According to some embodiments, the device further includes a torque transferring element configured to be placed within the elongated hollow member and to affect rotary motion of the rotatable cutting element, the torque transferring element comprising a core and at least one outer layer, the core comprising a bendable multi-stranded wire.

According to some embodiments, the torque transferring assembly further comprises a support structure configured to prevent helixing thereof.

According to some embodiments, the support structure comprises one or more rigid elements configured to define rigid and bendable sections along the torque transferring assembly/element, wherein sections of the torque transferring assembly/element, devoid of the rigid elements, are bendable. According to some embodiments, the one or more rigid elements comprise one or more tubular elements crimped over spaced apart sections of the torque transferring elongated members located in non-bend portions of the hollow elongated member.

Additionally or alternatively, the support structure comprises one or more bearings. According to some embodiments, the one or more bearings are configured to be positioned along a part of the torque transferring elongated member located in bend portions of the hollow elongated member.

According to some embodiments, the device further includes a torque transferring assembly configured to be placed within the elongated hollow member and to affect rotary motion of the rotatable cutting element. The torque transferring assembly includes a tube having torque transferring elements at its proximal and distal ends, wherein the torque transferring elements comprise a bendable core and at least one outer layer. According to some embodiments, the core is comprising a multi-stranded wire.

According to some embodiments, the device further includes a rotary actuator, placed within the handle configured to induce rotation motion to the torque transferring element/assembly.

According to some embodiments, the device further includes a control-interface configured to facilitate operation control over a rotation speed of said rotary actuator, and/or of said torque transferring element/assembly.

According to some embodiments, the device is a surgical drill.

According to some embodiments, the device further includes a third proximal bend.

According to some embodiments, there is provided a torque transferring assembly comprising: a torque transferring elongated member comprising a core and at least one outer layer, said core comprising a multi-stranded wire; a rotatable cutting element attached to a distal end and of said torque transferring elongated member; and a support structure configured to prevent helixing of said torque transferring elongated member when bent; wherein said torque transferring element/assembly is configured to facilitate rotary motion of the rotatable cutting element at least 15,000 RPM, at least 20,000 RPM, at least 40,000 and a torque of at least 4 Ncm.

According to some embodiments, the support structure comprises one or more rigid elements configured to define rigid and bendable sections along the torque transferring elongated member, wherein sections of the torque transferring elongated member, devoid of the rigid elements, are bendable.

According to some embodiments, the support structure comprises one or more tubular elements crimped over sections of said torque transferring elongated member.

Additionally or alternatively, the support structure comprises one or more bearings. According to some embodiments, the one or more bearings are configured to be positioned along a part of the torque transferring elongated member devoid of rigid elements so as to define an apex of the torque transferring elongated member when bent.

According to some embodiments, the torque transferring element/assembly is configured to facilitate rotary motion of the rotatable cutting element at least 40,000 RPM, and a torque of at least 4 Ncm.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

FIG. 1A schematically illustrates a side view of a device for hard tissue removal with a hollow elongated member with a proximal bend, a distal bend and a torque transferring assembly with rigid sections, according to some embodiments;

FIG. 1B is an enlarged view of a proximal end of the hollow elongated member of FIG. 1A, according to some embodiments, FIG. 1C is an enlarged view of a distal end of the hollow elongated member of FIG. 1A, according to some embodiments;

DETAILED DESCRIPTION

Figure 2A:
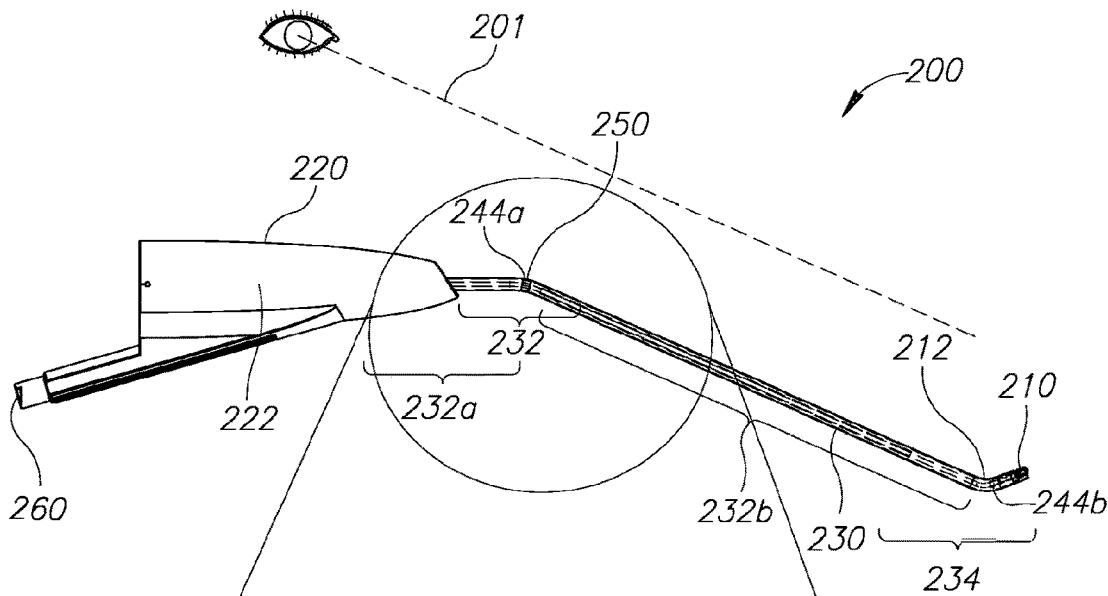
FIG. 2A schematically illustrates a side view of a device for hard tissue removal with a hollow elongated member with a proximal bend, a distal bend and a torque transferring assembly with rigid sections and a bearing element, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

According to some embodiments, there is provided a surgical device including an elongated hollow member extending having a proximal end and a distal end; wherein the distal end of the hollow member includes an opening, a torque transferring element/assembly, configured to be placed within the elongated hollow member, and a rotatable cutting element attached to said torque transferring element/assembly and extending through or positioned at the opening, wherein the proximal end of the hollow member includes at least one proximal bend configured to ensure that the part of the hollow member, which is distal to the proximal bend, is offset a central axis of part of the hollow member proximal to the proximal bend, wherein said torque transferring element/assembly is configured to affect rotary motion of the rotatable cutting element.

According to some embodiments, the device further includes a handle configured to facilitate operation and control of the device by an operator. According to some embodiments, the proximal bend of the hollow member is configured to ensure that the handle does not interfere with a surgeon's line of site to the cutting element.

According to some embodiments, the torque transferring element/assembly is configured to facilitate rotational speed of at least 15,000 RPM, at least 20,000 RPM, at least 25,000 RPM, at least 30,000 RPM or 40,000 RPM, and a torque of at least 4 Ncm Each possibility is a separate embodiment.

According to some embodiments, the torque transferring element/assembly may include one or more support structures configured to prevent helixing, pig-tailing and or looping thereof.

According to some embodiments, the term "helixing", "pig-tailing", "looping", "coiling" and "torqueing" may be used interchangeably and may refer to the inherent tendency of the torque transfer element to form a helix-like shape when a torque is being applied thereto. Helixing especially tends to cause failure and even tearing of the torque transfer element and/or layers thereof. While a sheering stress is associated with a sheering strain. i.e. rotation angle, the helixing phenomena might force that strain to be dispersed over a short length of the flexible torque transfer element, thus generating great local stresses which lead to a quick failure. Helixing is the most common cause for failure in flexible torque transferring elements.

According to some embodiments, the device is configured for bone and soft tissue removal. According to some embodiments, the device is configured to perform minimally invasive tissue resection, cutting, grinding and/or drilling. Each possibility is a separate embodiment. As used herein, the terms "tissue removal", "tissue cutting", "tissue grinding", "abrasive tissue cutting/grinding" may be interchangeable and include tissue reshaping, removal of excess tissue and/or tissue sharpening, or the like.

According to some embodiments, the device is configured to facilitate removal of hard and soft tissue from target locations/sites adjacent vertebrae and/or sites within/near the spinal canal.

According to some embodiments, the device is configured to treat and/or ameliorate spinal indications. According to some embodiments, the spinal indication is selected from: lumbar, thoracic, sacrum or cervical spinal stenosis, herniated disc, and/or bulged disc. According to some embodiments, the spinal indication is lumbar, thoracic, sacrum or cervical spinal stenosis. According to some embodiments, the tissue is an intervertebral disc tissue or bone tissue.

According to some embodiments, the device may advantageously facilitate minimal invasive treatment of lumbar, thoracic, sacrum or cervical spinal stenosis without removal of vertebrae or with minimal removal of the vertebrae. This as opposed to the common treatments in which vertebra and excess bone tissue is removed, and which necessitate fusion of adjacent vertebras in order to prevent spinal instability, and which are associated with long recuperation and pain. According to some embodiments, the instruments are configured for safe insertion between two adjacent vertebrae, allowing removal of excess osteophytes, bones and disc tissue. According to some embodiments, the device is configured for use in operations that include removal of soft tissue, such as a disc tissue, allowing treating a herniated or bulged disc. According to some embodiments, the device is configured for use in operations that include preparation of vertebras walls for fusion.

According to some embodiments, the device is configured for cutting tissue, such as disc tissue, by juxtaposing the device to the target location and introducing/contacting the cutter with the tissue to be cut. Advantageously, the device, according to some embodiments, may enable conducting procedures, such as disc removal, without the requirement of removing pieces of bone (such as the lamina) from the affected vertebra, thus allowing minimally invasive procedures for treating a herniated disc and contributing to higher success rates and faster recovery of the patients.

According to some embodiments, the device is delivered to the disc utilizing an accessory tool or instrument such as an endoscope or surgical microscope, a cannulated instrument configured to allow inserting the device through the disc without harming said disc, or similar procedures.

According to some embodiments, the dimensions of the device or any part thereof, are designed and shaped to facilitate a "low profile" safe insertion of the device in between two adjacent vertebrae and provide access to material present underneath vertebrae, which removal is desired.

According to some embodiments, the torque transferring element may be a cable. According to some embodiments, the torque transferring element may be a wire or a wire-like elongated bendable member. According to some embodiments, the torque transferring assembly may extend along the entire/majority of the length of the elongated hollow member. According to some embodiments, the torque transferring element may be a cable extending along the entire/majority of the length of the elongated hollow member.

As used herein the term "entire" may refer to 80%-100%, such as at least 80%, at least 85%, at least 90%, at least 95% or at least 98% of the length of the elongated hollow member. Each possibility is a separate embodiment. As used herein the term "majority" may refer to 55%-80% of the length of the elongated hollow member, such as about 55%, about 60%, about 65%, about 70%, about 75% or about 80%. Each possibility is a separate embodiment.

According to some embodiments, the torque transferring assembly's support structure may include rigid element(s)/section(s). According to some embodiments, the rigid element(s)/section(s) may extend along essentially the entire non-bent portions of the torque transferring assembly's or a majority thereof. According to some embodiments, the portion of the torque transferring element positioned/extending/ranging/encompassing the proximal bend (or other bends) may be devoid of rigid elements. According to some embodiments, the rigid element/section may overlay part of the one or more torque transferring elements. According to some embodiments, the rigid element(s)/section(s) may overlay the non-bent part(s) of the one or more torque transferring elements, or the majority of the non-bent part(s). As a non-limiting example, the rigid element(s)/section(s) may overlay the non-bent portion of a single torque transferring element, extending essentially along the entire length of the hollow elongated member. According to some embodiments, the rigid element(s)/section(s) may be tube elements crimped over or otherwise attached/affixed to the one or more torque transferring elements (non-bent portions). According to some embodiments, the rigid sections may include or be made from stainless steel (304, 316, 420) and/or polymeric materials (e.g. Nylon, HDPE, PTFE). According to some embodiments, the rigid elements may be shaped as tubes with an inner diameter of about 1 mm and outer diameter of about 1.5-3 mm (e.g. 1.46 mm or 2.5 mm)

and a wall thickness about 0-2-0.3 mm—e.g. 0.23 mm. Alternatively, the rigid elements may be square shaped. As a non-limiting example, the rigid elements may be square shaped and have internal dimensions of 1 mm×1 mm and outer dimensions of 1.46 mm×1.46 mm and an internal area of 1 mm$^2$ and outer area of 2.13 mm$^2$.

As used herein, the terms "non-bent part" or "non-bent portions" of the torque transferring assembly may refer to the part of the torque transferring assembly running through the essentially straight portion(s) of the hollow elongated member or a majority of the essentially straight portion(s), e.g. at least 95%, at least 90% or at least 85% of the essentially straight portion(s).

According to some embodiments, the rigid element/section may interconnect between two torque transferring elements. According to some embodiments, the rigid element(s)/section(s) may be hollow. According to some embodiments, the rigid element(s)/section(s) may be non-hollow.

According to some embodiments, the torque transferring assembly may include at least two torque transferring elements, positioned within a part of the hollow member, including bends. According to some embodiments, a first torque transferring element may be positioned within the part of the hollow member, including the proximal bend. According to some embodiments, a second torque transferring element may be positioned within the part of the hollow member, including the distal bend. According to some embodiments, the second torque transferring element of the torque transferring assembly may be positioned within the tip section of the hollow member.

According to some embodiments, the torque transferring element(s) may include a core and at least one outer layer, the core comprising a bendable multi-stranded wire. According to some embodiments, the multi-stranded wire of the core may include three strands. According to some embodiments, the multi-stranded wire of the core may include seven strands. According to some embodiments, the multi-stranded wire of the core may include nineteen strands. According to some embodiments, the multi-stranded wire of the core may include more than nineteen strands. According to some embodiments, the strands of the multi-stranded wire may be braided, twisted, interlaced or coiled. Each possibility is a separate embodiment.

According to some embodiments, the rigid element(s)/section(s) is configured to extend along at least a portion of the part of the elongated hollow member extending between the distal-most of the proximal bends and the proximal-most of the distal bends.

Additionally or alternatively, the torque transferring assembly's support structure may include a bearing such as a ball bearing, a friction bearing or any other suitable type of rotary support element configured to reduce friction between the torque transferring assemblys and the hollow elongated member. According to some embodiments, the bearing may be positioned at the apex of the one or more proximal bends and/or the one or more distal bends.

According to some embodiments, the at least two torque transferring elements may be the same or different. As a non-limiting example, the core of the first torque transferring element may be formed from 7 strands, whereas the core of the second torque transferring element may be formed from 19 strands. As another non-limiting example, the first torque transferring element may include 2 outer layers, whereas the second torque transferring element may include 3 outer layers. As another non-limiting example, the first torque transferring element may have a different length (e.g. longer) than the second torque transferring element.

According to some embodiments, the torque transferring assembly has high torsional rigidity and low bending rigidity.

According some embodiments, the core of the torque transferring element(s) is configured for maintaining high structural integrity and outer layers configured for maintaining high torsional rigidity. According some embodiments, each of the outer layers of the torque transferring element(s) may be configured to have mechanical properties in a direction opposite to the direction of the adjacent layer.

According to some embodiments, the torque transferring element(s) may be capable of supporting a (optionally bi-directional) rotational speed of at least 15,000 RPM, at least 20,000 RPM, at least 30,000 RPM, at least 40,000 RPM, at least 60,000 RPM, at least 70,000 RPM, at least 80,000 RPM, at least 90,000 RPM, or at least 100,000 RPM. According to some embodiments, the torque transferring element(s) may be capable of supporting a torque of at least 2 Ncm, at least 3 Ncm, at least 4 Ncm, at least 5 Ncm or at least 6 Ncm. Each possibility and combination of possibilities is a separate embodiment. As a non-limiting example, torque transferring element(s) may be capable of supporting a rotational speed of 80,000 RPM, at a torque of 5 Ncm.

According to some embodiments, the torque transferring element extends from a motor optionally positioned within the handle of the device. According to some embodiments, the torque transferring element/assembly is attached to the proximal end of the elongated hollow member. According to some embodiments, the torque transferring element/assembly is attached to the rotatable cutting head and may be configured to transmit rotational (optionally bidirectional) and optionally forward/backward motion to the rotatable cutting head.

According to some embodiments, the torque transferring element/assembly may be configured for high torsional rigidity and low bending rigidity, potentially enabling the torque transferring element to rotate at high speed while bent, advantageously even at a small radius of curvature. Having a low bending rigidity provides low bending-related stress and better resistance to fatigue caused by high rotation speed and/or high rotation torque.

According to some embodiments, the torque transferring element(s) may be fabricated from stainless-steel wires (also referred to herein as strands), twisted (braided or coiled) into a rope, constituting a core. As a non-limiting example, the torque transferring element(s) may be fabricated from seven 304V stainless-steel wires (each having a diameter of, for example, 0.084 mm) twisted into a rope. Several layers e.g. 3 layers, may then be wound around the rope core. Each successive layer (e.g coil) may optionally be wound in the opposite direction of the layer which precedes it. As a non-limiting example, the first outer layer (the layer closest to the core) may include 5 wires (with a diameter of e.g. 0.12 mm each) coiled, stranded or twisted in a first direction (e.g. clockwise), the middle layer may, for example, include 5 wires (with a diameter of e.g. 0.14 mm each) coiled, stranded or twisted in a direction opposite the first outer layer (e.g. counter clockwise), and the third outer layer may, for example, include 5 wires (with a diameter of e.g. 0.16 mm each) coiled, stranded or twisted in a direction opposite the middle outer layer.

According to some embodiments, the torque transferring element/assembly has an outer diameter of, for example, 0.3 mm to 5 mm, e.g. 0.5 mm or 1 mm or 1.5 mm or 3 mm.

According to some embodiments, the torque transferring element(s) may have the following physical properties: bending angle: 0-90 degrees, rotation speed: 15,000-60,000 rpm, bending radius: 4.5-9 mm, diameter: 0.5 mm-3 mm, and length 5-300 mm (for example, 5-50 mm, 40-200 mm or about 40 mm).

According to some embodiments, the torque transferring element(s) may have the following physical properties: bending angle: 0-90 degrees, rotation speed: 15,000-80,000 rpm, bending radius: 2-18 mm, diameter: 1-7 mm, and length: 1-40 mm.

According to some embodiments, the torque transferring element(s) may have the following physical properties: bending angle: 50-80 degrees, rotation speed: 15,000-80,000 rpm, bending radius: 6-7 mm, diameter: 3-5 mm, and length: 9-30 mm.

According to some embodiments, the at least one proximal bend of the hollow member is configured to ensure visualization of the cutter and/or the tissue adjacent to the distal end of the device, when in use. According to some embodiments, the at least one proximal bend of the hollow member is configured to ensure that the handle, the surgeon's hand, surgical microscope and/or the endoscope do not impair the visualization of the cutter and/or the tissue adjacent to the distal end of the device, when in use. According to some embodiments, the at least one proximal bend of the hollow member enables utilizing a surgical microscope, such as a surgical microscope that has a short focal length, this since the microscope may be located parallel to the shaft and close to the surgical site while avoiding that the handle interferes with the microscope and the line of sight.

As used herein, the term "proximal" with referral to the elongated hollow member refers to part of the hollow member closest to the handle. According to some embodiments, the term may refer to the ⅓ of the hollow member closest to the handle.

As used herein, the term "distal" with referral to the elongated hollow member refers to part of the hollow member carrying the rotatable cutter and adjacent the target tissue. According to some embodiments, the distal end may include a tip section. According to some embodiments, the distal end may refer to the ⅓ of the hollow member furthest away from the handle.

As used herein, the terms "tip" and "tip section" may refer to the engaging portion of the device, including the cutter and at least part of the distal end of the elongated hollow member. According to some embodiments, the term tip refers to the part of the elongated hollow member (and the torque transferring element placed therein) extending from the distal bend to the distal extremity thereof. According to some embodiments, the tip may have a length of 5-16 mm, for example, about 11 mm. According to some embodiments, the term tip may refer to a part of the device configured to be inserted between bone tissue. According to some embodiments, the tip is configured to be stationary during operation, at least with regards to axial rotation.

According to some embodiments, the term "at least one", when referring to proximal bends of the hollow member, may be a single proximal bend. Alternatively, the at least one proximal bend may include 2, 3, 4, 5 or more proximal bends. Each possibility is a separate embodiment.

According to some embodiments, the at least one proximal bend has a bending angle of up to 90 degrees relative to the central axis of said handle. According to some embodiments, the at least one proximal bend has a bending angle of up to 80 degrees relative to the central axis of said handle. According to some embodiments, the at least one proximal bend has a bending angle of up to 70 degrees relative to the central axis of said handle. According to some embodiments, the at least one proximal bend has a bending angle of up to 60 degrees relative to the central axis of said handle.

According to some embodiments, the at least one proximal bend has a bending angle of 10-90 degrees relative to the central axis of said handle. According to some embodiments, the at least one proximal bend has a bending angle of 10-80 degrees relative to the central axis of said handle. According to some embodiments, the at least one proximal bend has a bending angle of 20-80 degrees relative to the central axis of said handle. According to some embodiments, the at least one proximal bend has a bending angle of 20-60 degrees relative to the central axis of said handle.

According to some embodiments, the at least one proximal bend has a bending radius of less than 15 mm, less than 12 mm, less than 10 mm, less that 7 mm or less than 5 mm. Each possibility is a separate embodiment. According to some embodiments, the at least one proximal bend has a bending radius in the range of 5 mm-15 mm.

According to some embodiments, the hollow member includes at least two proximal bends. According to some embodiments, the hollow member includes at least three proximal bends. According to some embodiments, the hollow member includes at least four proximal bends. According to some embodiments, the hollow member may include a plurality of proximal bends (e.g. 5 or more bends). According to some embodiments, the bends may be in a same plane. According to some embodiments, the bends (or some thereof) may be in a different plane.

According to some embodiments, by being double bended, the part of the hollow member downstream to the first and second proximal bends will be substantially parallel (e.g. +/−10 degrees) to the central axis of said handle. Advantageously, this may ease the maneuvering of the device by the operator, while maintaining line of sight.

According to some embodiments, the at least two proximal bends may have a bending angle of up to 90 degrees relative to the central axis of the handle. According to some embodiments, the at least two proximal bends may have a bending angle of up to 80 degrees relative to the central axis of the handle. According to some embodiments, the at least two proximal bends may have a bending angle of up to 70 degrees relative to the central axis of the handle. According to some embodiments, the at least two proximal bends may have a bending angle of up to 60 degrees relative to the central axis of the handle. According to some embodiments, the at least two proximal bends may have a bending angle of 10-90 degrees relative to the central axis of the handle. According to some embodiments, the at least two proximal bends may have a bending angle of 10-80 degrees relative to the central axis of the handle. According to some embodiments, the at least two proximal bends may have a bending angle of 20-80 degrees relative to the central axis of the handle. According to some embodiments, the at least two proximal bends may have a bending angle of 20-60 degrees relative to the central axis of the handle. According to some embodiments, the bending angle of the at least two proximal bends may be the same or different.

According to some embodiments, the at least two proximal bends may have a bending radius of less than 15 mm, less than 12 mm, less than 10 mm, less that 7 mm or less than 5 mm. Each possibility is a separate embodiment. According to some embodiments, the at least two proximal bends may have a bending radius in the range of 5 mm-15 mm.

According to some embodiments, the bending angle of the at least two proximal bends may be the same or different.

According to some embodiments, the elongated hollow member may include at least one distal bend, such as 1,2, 3 or more distal bends. Each possibility is a separate embodiment. According to some embodiments, the distal bends may be in a same plane. According to some embodiments, the distal bends (or some thereof) may be in a different plane. According to some embodiments, the elongated hollow member may include a single distal bend.

Additionally or alternatively, the device may include one or more medial bends positioned between the proximal and distal ends of the hollow elongated member, such as, but not limited to, around halfway the length of the hollow elongated member or between the ⅓ defining the proximal end and the ⅓ defining the distal end. According to some embodiments, the medial bends may be in a same plane. According to some embodiments, the medial bends (or some thereof) may be in a different plane. Advantageously, such medial bends may ensure an unhindered line of site when utilizing the device in robotic/robot assisted surgeries.

According to some embodiment, the device may include only proximal bends, only distal bends, or only distal bends. Alternatively, the device may include both proximal, distal and medial bends. Each possibility is a separate embodiment.

According to some embodiments, the at least one distal bend may have a bending angle of up to 90 degrees relative to the central axis, the part of the hollow member distal to the at least one proximal bend. According to some embodiments, the at least one distal bend may have a bending angle of up to 80 degrees relative to the part of the hollow member distal to the at least one proximal bend. According to some embodiments, the at least one distal bend may have a bending angle of up to 70 degrees relative to the part of the hollow member distal to the at least one proximal bend. According to some embodiments, the at least one distal bend may have a bending angle of up to 60 degrees relative to the part of the hollow member distal to the at least one proximal bend. According to some embodiments, the at least two proximal bends may have a bending angle of 10-90 degrees relative to the central axis of said handle. According to some embodiments, the at least one distal bend may have a bending angle of 10-80 degrees relative to the part of the hollow member distal to the at least one proximal bend. According to some embodiments, the at least one distal bend may have a bending angle of 20-80 degrees relative to the part of the hollow member distal to the at least one proximal bend. According to some embodiments, the at least one distal bend may have a bending angle of 20-60 degrees relative to the part of the hollow member distal to the at least one proximal bend. According to some embodiments, the bending angle of the at least one distal bend may be the same or different from the bending angle of the at least one proximal bend.

According to some embodiments, the at least one distal bend may have a bending radius of less than 15 mm, less than 12 mm, less than 10 mm, less that 7 mm or less than 5 mm. Each possibility is a separate embodiment. According to some embodiments, the at least one distal bend may have a bending radius in the range of 5 mm-15 mm, 2-12 mm or 6-10 mm. Each possibility is a separate embodiment. As a non-limiting example, the bending ratio may be 9 mm. According to some embodiments, the bending angle of the at least one distal bend may be the same or different from the bending radius of the at least one proximal bend.

According to some embodiments, the distance between the distal bend and the opening is less than 30 mm. According to some embodiments, the distance between the distal bend and the opening is less than 25 mm. According to some embodiments, the distance between the distal bend and the opening is less than 20 mm. According to some embodiments, the distance between the distal bend and the opening is less than 15 mm. According to some embodiments, the distance between the distal bend and the opening is less than 10 mm. According to some embodiments, the distance between the distal bend and the opening is in the range of 1-20 mm. According to some embodiments, the distance between the distal bend and the opening is in the range of 3-10 mm. As a non-limiting example, the distance between the distal bend and the opening may be 8 mm.

According to some embodiments, the distal end may be parallel to the central axis of the handle. As a non-limiting example, the hollow member may include a single proximal bend and a single distal bend configured such that the part of the hollow member extending between the proximal and distal bends be offset the central axis of the handle, whereas the part of the hollow member extending from the distal bend to the distal extremity of the hollow member be parallel to the central axis of the handle.

According to some embodiments, the distal end may be offset the central axis of the handle. As a non-limiting example, the hollow member may include two proximal bends and a single distal bend configured such that the part of the hollow member extending between the proximal bends and the distal bend be parallel to the central axis of the handle, whereas the part of the hollow member extending from the distal bend to the distal extremity of the hollow member be offset the central axis of the handle.

According to some embodiments, the elongated hollow member may be, for example, 30-300 mm, 50-200, 50-150 mm, or 75-125 mm in length, as measured from the handle to the distal tip. Each possibility is a separate embodiment. As a non-limiting example, the elongated hollow member may have a length of 104 mm.

According to some embodiments, the elongated hollow member may have a circular or oval cross section with an external diameter of, for example, 2-10 mm, 2-5 mm, 2.5-4 mm or 3-3.5 mm. Each possibility is a separate embodiment. As a non-limiting example, the elongated hollow member may have an external diameter of 3.2 mm. The diameter and/or cross sectional shape of the elongated device body may be constant along its length or may vary, for example, from a larger diameter at a proximal end to a smaller diameter at a distal end or vice versa.

According to some embodiments, the elongated hollow member may have a lumen with a diameter of 1-4 mm or 2-3 mm. Each possibility is a separate embodiment. As a non-limiting example, the elongated hollow member may have an internal diameter of 2.8 mm. According to some embodiments, the internal lumen may be sized and shaped for intimately housing a torque transferring elements/assembly, as further described hereinbelow. According to some embodiments, the diameter of the internal lumen may be 30-400% larger than the external diameter of the torque transferring elements/assembly to ensure that at least a flexible portion of the torque transferring elements/assembly does not kink or warp within the lumen. According to some embodiments, the lumen may be centered within the elongated hollow member.

According to some embodiments, the elongated hollow member may be fabricated from any material used in surgical devices, including, for example, stainless-steel, cobalt chrome, Nickel Titanium alloy (Nitinol), titanium, a polymer, and the like. The various device components may be fabricated using well known approaches such as braiding, coiling, stranding, casting, extrusion, machining, 3D printing and the like.

According to some embodiments, the rotatable cutter may include or be a rotary cutting blade. According to some embodiments, the rotatable cutter may include or be a plurality of jointed cutting elements, such as a plurality of cutting discs, and/or cutting elements such as diamond powder.

According to some embodiments, the rotatable cutter may be cylindrical, with circumferential cutting properties. According to some embodiments, the rotatable cutter may be cylindrical, with radial circumferential cutting properties (lateral). According to some embodiments, the rotatable cutter may be cylindrical with forward/distal circumferential cutting properties.

According to some embodiments, the rotatable cutter may be at least partially coated with diamonds. According to some embodiments, the rotatable cutter may be at least partially embedded with blades.

According to some embodiments, the rotatable cutter may be fabricated from, for example, 17.4 pH (thermal-hardened) stainless steel or stainless steel 420; for example, 2.5 mm Outer Diameter with, for example, 2-4 spiral flutes (lead angle, for example, 26 Deg, depth, for example, 0.75 mm, width, for example, 0.8 mm) each having a sharp edge forming a blade. According to some embodiments, the rotatable cutter may be in a shape of a disc comprising cutting edges at its perimeter. According to some embodiments, the rotatable cutter may include two opposite longitudinal straight edges and two opposite lateral cutting edges. According to some embodiments, the length of the rotatable cutter portion may vary depending on use from 1 mm-100 mm (e.g. 2 mm).

According to some embodiments, the rotatable cutter may be configured to rotate axially at rotation speed of up to 100,000 rounds per minute (RPM). According to some embodiments, the rotatable cutter may be configured to rotate axially at a rotation speed in the range of 5,000 RPM to 100,000 RPM. According to some embodiments, the rotatable cutter may be configured to rotate axially at a rotation speed in the range of 15,000 RPM to 70,000 RPM. According to some embodiments, the rotatable cutter may be configured to rotate axially at a rotation speed in the range of 20,000 RPM to 50,000 RPM.

According to some embodiments, the torque provided to the rotatable cutter may be in the range of 1-15 N*cm. According to some embodiments, the torque provided to the rotatable cutter may be in the range of 2-10 N*cm. According to some embodiments, the torque provided to the rotatable cutter may be in the range of 6-8 N*cm. According to some embodiments, the torque values refer to dynamic torque values, specifically at the rotation speeds of the rotatable cutter as provided in various embodiments.

According to some embodiments, the torque and/or rotation speed may be controlled by the operator of the device/instrument.

According to some embodiments, the rotatable cutter may be configured to facilitate at least one of: lateral cutting, posterior tissue cutting, or forward cutting. Each possibility is a separate embodiment.

According to some embodiments, the elongated hollow member may include a protective shield. According to some embodiments, the protective shield may extend from the distal end of the elongated hollow member to at least partially cover the circular action cutter and/or to at least partially cover the distal end of the device. According to some embodiments, the protective shield extends from the distal end of said elongated hollow member to at least partially cover the circular action cutter and/or to at least partially cover the distal end of the device. According to some embodiments, the protective shield may be configured to separate between the rotatable cutter and tissue distal and below the rotatable cutter, thereby mitigating the risk of impacting the tissue due to rotation of the rotatable cutter. According to some embodiments, the protective shield may be configured to mechanically separate between two tissue layers to facilitate introduction of the rotatable cutter to target tissue. According to some embodiments, the protective shield may be circular or semi-circular or dome shaped, with a diameter in the range of 3 mm to 10 mm. According to some embodiments, the protective shield may be circular or semi-circular or dome shaped, with a diameter in the range of 1 mm to 4 mm. According to some embodiments, the protective shield may be circular or semi-circular or dome shaped, with a diameter in the range of 5 mm to 7 mm. According to some embodiments, the protective shield may be circular or semi-circular or dome shaped, with a diameter of approximately 6 mm. According to some embodiments, the protective shield is configured to shield off the distal end of the rotatable cutter. According to some embodiments, the protective shield may be essentially perpendicular to the longitudinal axis of the distal end and/or of the circular action cutter. According to some embodiments, the protective shield may be positioned at an angle of 0-90 degrees, 0-60 degrees, 10-90 degrees, 60-90 degrees or any other suitable angle or range of angles within the range of 0-90 degrees, relative to the longitudinal axis of the distal end and/or of the circular action cutter. According to some embodiments, the protective shield is configured to shield off the distal end of the rotatable cutter. According to some embodiments, the protective shield may be essentially perpendicular to the longitudinal axis of the distal end and/or of the circular action cutter. According to some embodiments, the protective shield may be positioned at an angle of 0-90 degrees, 0-60 degrees, 10-90 degrees, 60-90 degrees or any other suitable angle or range of angles within the range of 0-90 degrees, relative to the longitudinal axis of the distal end and/or of the circular action cutter.

According to some embodiments, the device may further include an irrigation system for irrigating the tissue while drilling/cutting, which is advantageous in preventing overheating of the target tissue or surrounding tissues. According to some embodiments, the elongated hollow member may include an irrigation lumen. According to some embodiments, the proximal end of the elongated hollow member may include a seal for sealing the irrigation lumen. According to some embodiments, the seal may be composed of a temperature resistant material having a Shore durometer value of, for example, 50 A or less. According to some embodiments, the temperature resistant material may be silicon rubber, self-lubricating silicon rubber or self-lubricating silicon rubber including silicon oil having a temperature independent viscosity.

According to some embodiments, the device may further include a suction pump for removing tissue grinds and/or fluids from the cutting site.

According to some embodiments, the handle may house a drive and, optionally, a motor, as well as electrical circuitry. According to some embodiments, the housing may include an adaptor configured to allow connection to different types of surgical motors. According to some embodiments, the handle may be configured for allowing a user to manipulate the device and operate the motor driven rotatable cutting head. In that respect, the handle may be shaped substantially as an inverted cone with a length of, for example, 75-105 mm and a proximal diameter of, for example, 20-30 mm and a distal diameter of, for example, 5-15 mm. According to some embodiments, the handle may be fabricated as a shell composed of one or more cast, machined or injection-molded pieces. According to some embodiments, the handle may include a user interface for operating the motor, setting motor parameters (for example, the rotation speed and direction of rotation, etc.), setting cutting time, operating and setting irrigation and/or suction parameters, as well as controlling adjunct devices such as a neuro-stimulation device. According to some embodiments, the handle may be designed and configured such that a surgeon maintains a clear line-of-site along the device, helping the surgeon to monitor progress while cutting some tissue and avoiding tissues not targeted for cutting.

According to some embodiments, the user interface may further include a display for displaying various parameters related to the motor or to irrigation, as well as information related to the cutting head and multi-stranded wire such as temperature, mechanical integrity, cutting head position and the like, and information related to adjunct device (for example electrodes for neuro-monitoring) used during a procedure.

According to some embodiments, the device may be disposable in its entirety. According to some embodiments, parts of the device are disposable. According to some embodiments, the tip is disposable. According to some embodiments, the rotatable cutter is disposable. According to some embodiments, the torque transferring element/assembly is disposable.

According to some embodiments, the surgical tip (at the distal end of the elongated hollow member, is configured to have at least two operation modes, one of which being an insertion mode (or non-active state), and the other being an operation/cutting mode (or active state). According to some embodiments, in the insertion mode, the rotatable cutter is positioned to not protrude out from the opening to lower the risk of impacting tissues during insertion.

According to some embodiments, the device may be connected to or connectable to an imaging plate comprising one or more navigation elements configured to allow determining the spatial orientation and/or coordinates of the device, when in use. According to some embodiments, the navigation elements may be made of a material allowing their visualization using different visualization techniques.

Reference is now made to FIG. 1A-FIG. 1C, which schematically illustrate a device 100 for hard tissue removal, with a single proximal bend 150, according to some embodiments. Device 100 includes a handle 120 connected to an elongated hollow member 130 having a proximal end 132 and a distal end 134. Distal end 134 includes a rotatable cutting tip 110 for surgical tissue cutting and a distal bend 112 configured to ensure convenient positioning of rotatable cutting tip 110 into a desired target location (e.g. between adjacent vertebras or underneath a vertebra). Proximal bend 150 serves to ensure that part of elongated hollow member 130 distal to proximal bend 150 is offset of handle 120, thus ensuring a surgeon's unhindered line of site 101 to rotatable cutting tip 110, when holding handle 120. Advantageously, proximal bend 150 enables utilizing surgical tools, such as, but not limited to, surgical microscopes (not shown). This since the microscope may be located parallel to elongated hollow member 130 and close to rotatable cutting tip 110 while avoiding that handle 120 interferes with the microscope and line of sight 101. Elongated hollowed member 130 includes a torque transferring assembly 140 extending from a motor 122, here positioned within handle 120. Torque transferring assembly 140 is configured to bring about rotary motion of rotatable cutting tip 110, while maintaining a high structural integrity despite its multiple bent configuration.

Torque transferring assembly 140 includes rigid sections 142a and 142b extending along the majority of straight portions 132a and 132b within elongated hollowed member 130 and bendable sections 144a and 144b of torque extending along and within proximal bend 150 and distal bend 112, respectively. According to some embodiments, bendable sections 144a and 144b extend along the entire length of proximal bend 150 and distal bend 112, respectively. According to some embodiments, bendable sections 144a and 144b may extend along a portion longer than the length of proximal bend 150 and distal bend 112, respectively (e.g. about 2%-5% longer than the length of proximal bend 150 and distal bend 112, respectively). According to some embodiments, bendable sections 144a and 144b may be separate elements, interconnected by rigid section 142b. Alternatively, torque transferring elements 144a and 144b may be part of a single continuous element (not visible in its entirety) extending along the length of torque transferring assembly 140, in which case, rigid sections 142a and 142b are crimped over torque transferring assembly 140 such that bendable sections 144a and 144b remain exposed. Rigid sections 142a and 142b are configured to ensure that helixing of torque transferring assembly 140 is prevented/inhibited, while torque transferring elements 144a and 144b facilitate high rotational speed and a torque.

According to some embodiments, handle 120 includes an operational input 160 utilized, for example, for providing electric energy for operating device 100, introducing additional surgical instruments, connecting to sensors, cameras, or the like.

Figure 2B:
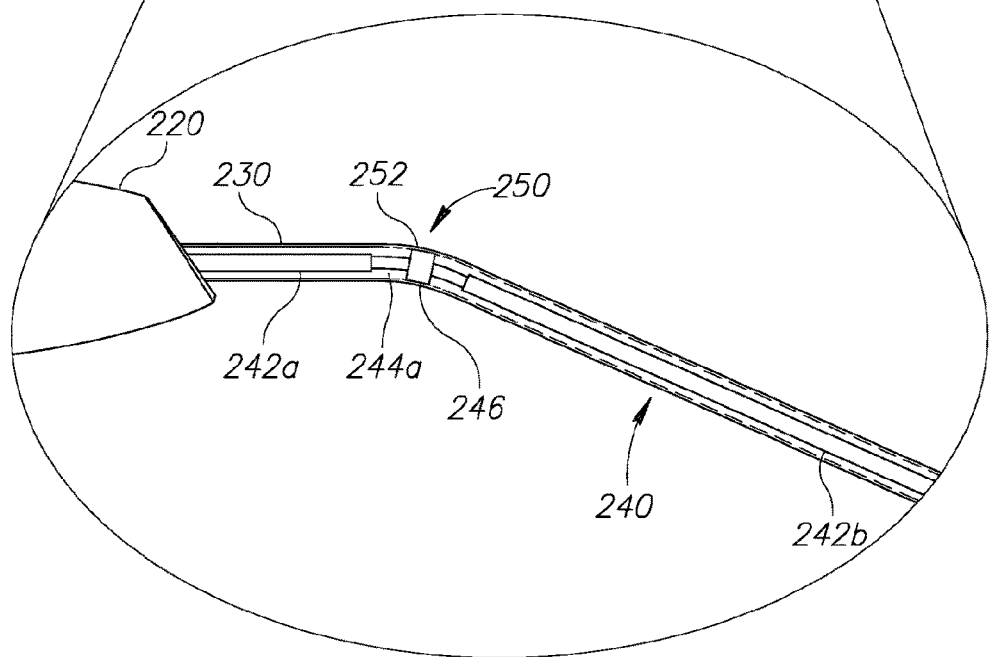
FIG. 2B is an enlarged view of a proximal end of the hollow elongated member of FIG. 2A, according to some embodiments.

Reference is now made to FIG. 2A-FIG. 2B, which schematically illustrate a device 200 for hard tissue removal, with a single proximal bend 250, according to some embodiments. Device 200 includes a handle 220 connected to an elongated hollow member 230 having a proximal end 232 and a distal end 234. Distal end 234 includes a rotatable cutting tip 210 for surgical tissue cutting and a distal bend 212 configured to ensure convenient positioning of rotatable cutting tip 210 into a desired target location (e.g. between adjacent vertebras or underneath a vertebra). Proximal bend 250 which serves to ensure that part of elongated hollow member 230 distal to bend 250 is offset handle 220, thus ensuring a surgeon's unhindered line of site 201 to rotatable cutting tip 210, when holding handle 220. Advantageously, proximal bend 250 enables utilizing surgical tools, such as, but not limited to, surgical microscopes (not shown). This since the microscope may be located parallel to elongated hollow member 230 and close to rotatable cutting tip 210 while avoiding that handle 220 interferes with the microscope and line of sight 201. Elongated hollow member 230 includes therein a torque transferring element/assembly (not shown).

According to some embodiments, handle 220 includes an operational input 260 utilized, for example, for providing electric energy for operating device 200, introducing additional surgical instruments, connecting to sensors, cameras, or the like.

Elongated hollowed member 230 includes a torque transferring assembly 240 extending from a motor 222 here positioned within handle 220. Torque transferring assembly 240 is configured to bring about rotary motion of rotatable cutting tip 210, while maintaining high structural integrity despite the multiple bent configuration.

Torque transferring assembly 240 includes rigid sections 242a and 242b extending along the majority of straight portions 232a and 232b within elongated hollowed member 230 and bendable section 244a and 244b extending along and within proximal bend 250 and distal bend 212, respectively. According to some embodiments, the bendable sections 244a and 244b may extend along the entire length of proximal bend 250 and distal bend 212, respectively. According to some embodiments, bendable sections 244a and 244b may extend along a portion longer than the length of proximal bend 250 and distal bend 212, respectively (e.g. about 2%-5% longer than the length of proximal bend 250 and distal bend 212, respectively). According to some embodiments, bendable sections 244a and 244b may be separate elements, interconnected by rigid section 242b. Alternatively, bendable sections 244a and 244b may be part of a single continuous element (not visible in its entirety) extending along the length of torque transferring assembly 240, in which case, rigid sections 242a and 242b are crimped over or otherwise overlaying torque transferring assembly 240 such that bendable sections 244a and 244b remain exposed. Rigid sections 242a and 242b are configured to ensure that helixing of torque transferring assembly 240 is prevented/inhibited, while torque transferring elements 244a and 244b facilitate high rotational speed and a torque.

Torque transferring assembly 240 further includes a bearing support element 246 positioned at apex 252 of proximal bend 250. Bearing support element 246 is configured to reduce friction between torque transferring assembly 240 and hollow elongated member 230 and may be any suitable type of bearing element, such as, but not limited to, a ball bearing or a friction bearing.

Figures 3A, 3B:
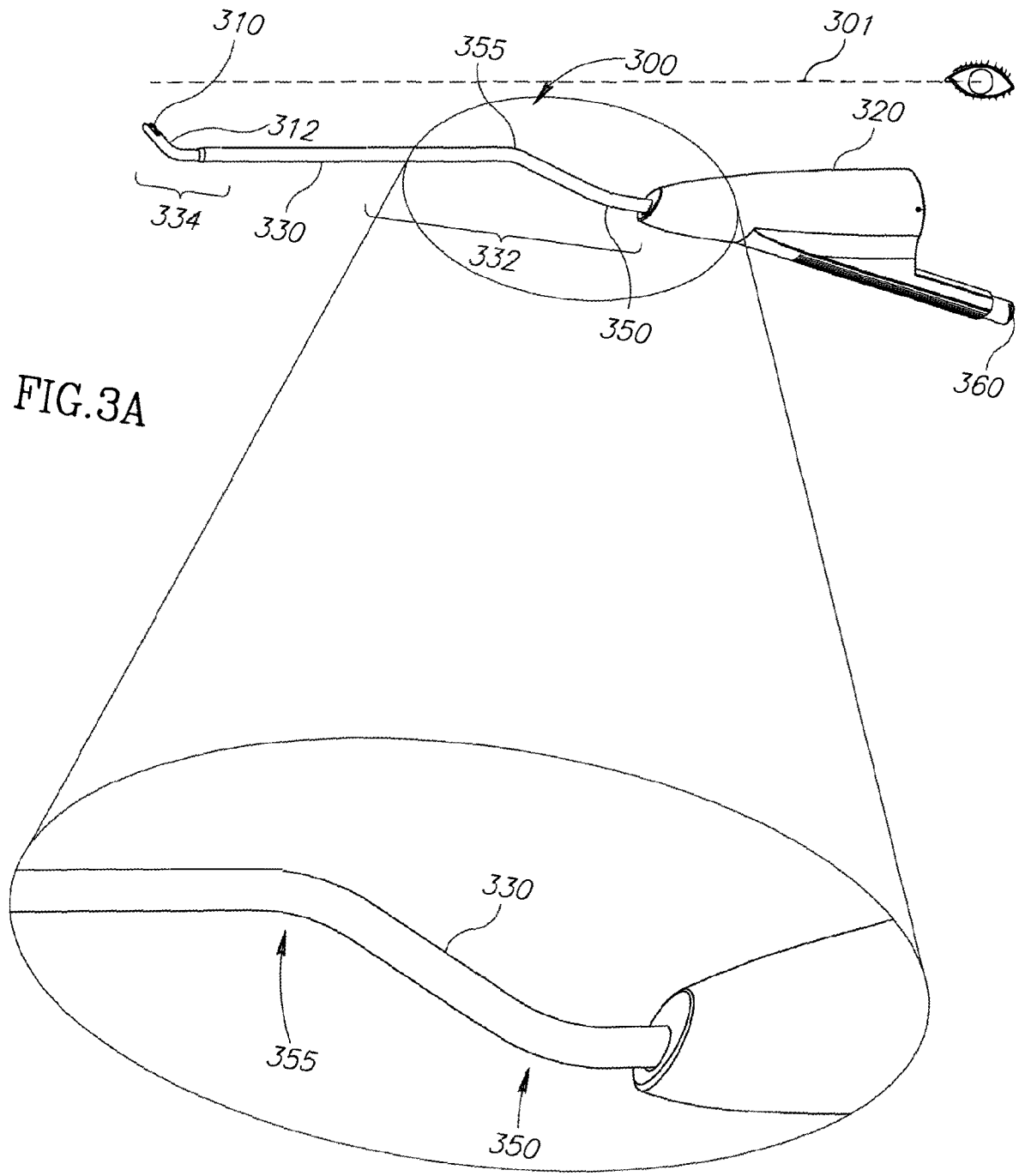
FIG. 3A schematically illustrates a side view of a device for hard tissue removal with a hollow elongated member with two proximal bends, according to some embodiments.
FIG. 3B is an enlarged view of a proximal end of the hollow elongated member of FIG. 3A, according to some embodiments.

Reference is now made to FIG. 3, which schematically illustrates a device 300 for hard or soft tissue removal, with two proximal bends 350 and 355, according to some embodiments. Device 300 includes a handle 320 connected to an elongated hollow member 330 having a proximal end 332 and a distal end 334. Distal end 334 includes a rotatable cutting tip 310 for surgical tissue cutting and a distal bend 312 configured to provide convenient positioning of rotatable cutting tip 310 at a desired target location (e.g. between adjacent vertebras or underneath a vertebra). Proximal bend 350 serves to ensure that elongated hollow member 330 be offset handle 320, thus ensuring a surgeon's unhindered line of site 301 to rotatable cutting tip 310, when holding handle 320. Proximal end 332 further includes a second proximal bend 355 configured to facilitate that part of elongated hollow member 330 distal to proximal bend 350 be parallel to the part of elongated hollow member 330 proximal to proximal bend 350. This prevents handle 320 from concealing cutting tip 310 and ensures visibility of cutting tip 310 and of target tissue during the procedure. Elongated hollow member 330 includes therein a torque transferring element, essentially similar to torque transferring element 140 of FIG. 1A-FIG. 1C. According to some embodiments, handle 320 includes an operational input 360 utilized, for example, for providing electric energy for operating the device, introducing additional surgical instruments, connecting to sensors, cameras, or the like.

Figure 4:
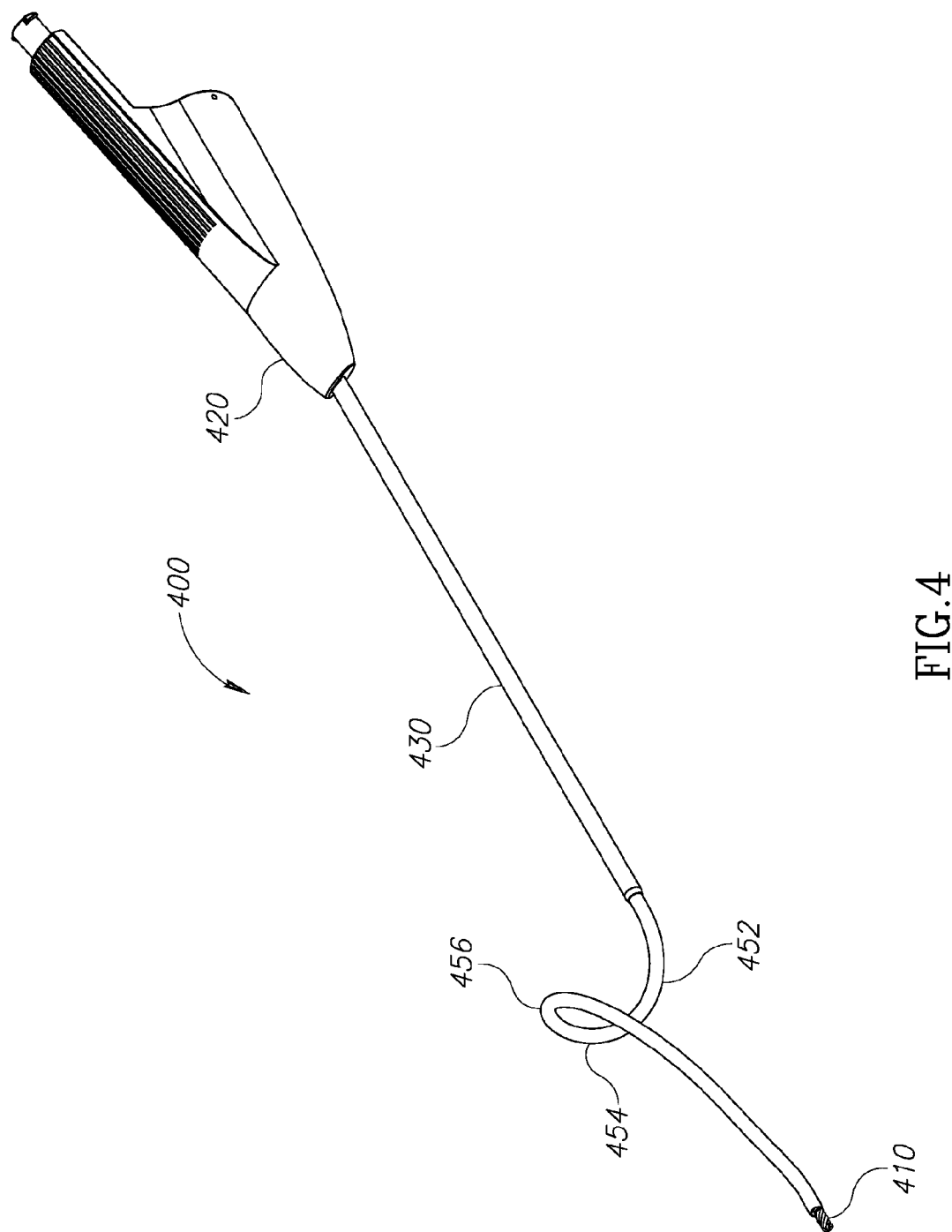
FIG. 4 schematically illustrates a side view of a device for hard tissue removal with a hollow elongated member with medial bends, according to some embodiments.

Reference is now made to FIG. 4 which schematically illustrates a side view of a device 400 for hard tissue removal with a hollow elongated member 430 extending from handle 420. Hollow member 430 includes medial bends 452, 454 and 456, positioned essentially at a middle part of hollow elongated member 430. Advantageously, medial bends 452, 454 and 456 are configured to ensure an unhindered line of site to rotatable cutting element 410, in particular when utilizing device 400 for robotic/robot assisted surgeries. Device 400 is here shown as being devoid of proximal and distal bends, however configurations including both medial and proximal and/or distal bends are also applicable and within the scope of this disclosure. Similarly, hollow elongated member 430 is here depicted with three medial bends; however, other configurations including less or more medial bends are also envisaged and within the scope of this disclosure.

Figure 5A:
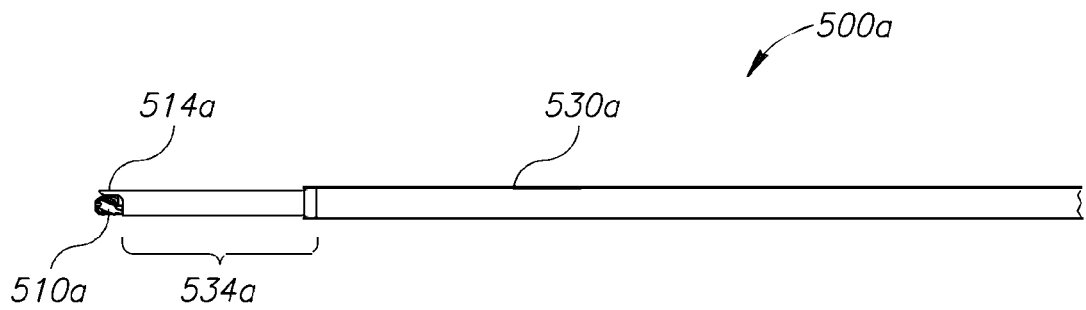
FIG. 5A is an enlarged view of a distal end of a hollow elongated member devoid of a distal bend, according to some embodiments.

Reference is now made to FIG. 5A, which schematically illustrates a distal end 500a of a hollow elongated member 530a of a device for tissue removal (as disclosed herein), devoid of a distal bend, according to some embodiments. Due to the absence of a distal bend, tip section 534a, including rotatable cutting tip 510a, is coextensive with hollow elongated member 530a. Tip section 534a further includes a shield 514a configured to shield one side of rotatable cutting tip 510a, thus minimizing collateral damage to adjacent tissue.

Figure 5B:
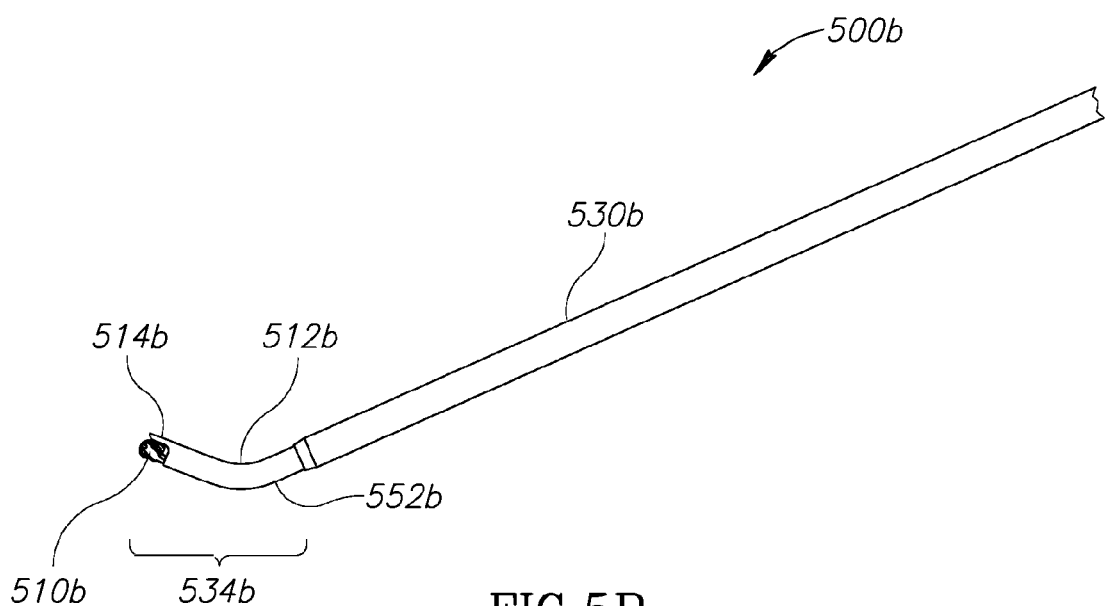
FIG. 5B is an enlarged view of a distal end of a hollow elongated member having a distal bend and a shield opposite the apex of the distal bend, according to some embodiments.

Reference is now made to FIG. 5B, which schematically illustrates a distal end 500b of a hollow elongated member 530b of a device for tissue removal (as disclosed herein) having a distal bend 512b. Due to distal bend 512b, tip section 534b, and thus rotatable cutting tip 510b, of hollow elongated member 530b is offset the longitudinal axis of hollow elongated member 530b of distal end 500b thus facilitating access to difficult to access areas, such as between and underneath vertebrae. Tip section 534b further includes a shield 514b covering a part of rotatable cutting tip 510b facing opposite apex 552b of bend 512b, thus shielding tissue positioned beneath tip section 534b.

Figure 5C:
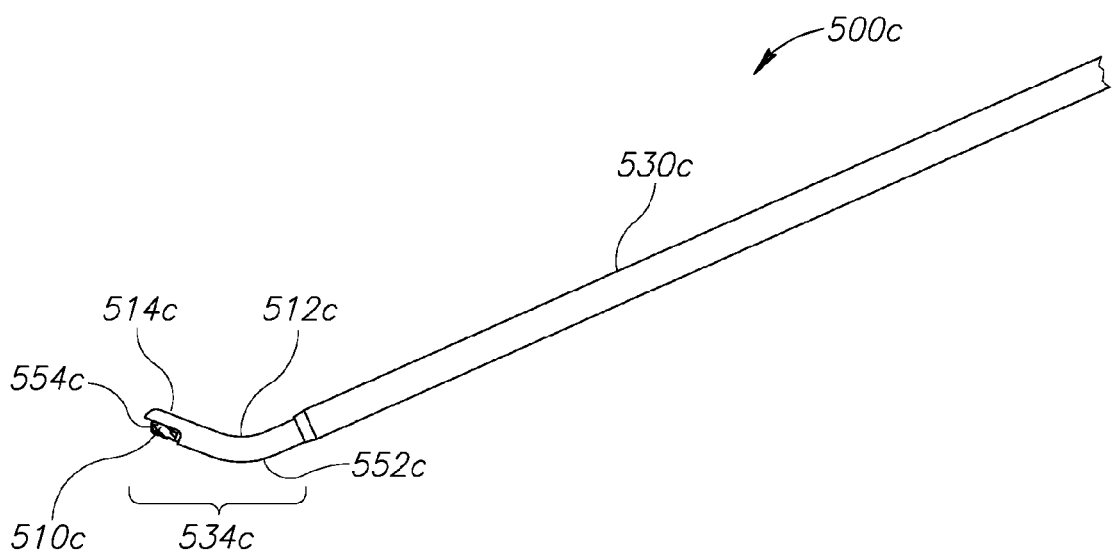
FIG. 5C is an enlarged view of a distal end of a hollow elongated member having a distal bend and a front shield opposite the apex of the distal bend, according to some embodiments.

Reference is now made to FIG. 5C, which schematically illustrates a distal end 500c of a hollow elongated member 530c of a device for tissue removal (as disclosed herein) having a distal bend 512c. Due to distal bend 512c, tip section 534c, and thus rotatable cutting tip 510c, of hollow elongated member 530c, is offset the longitudinal axis of hollow elongated member 530c of distal end 500c, thus facilitating access to difficult to access areas, such as between and underneath vertebrae. Tip section 534c further includes a shield 514c covering a part of rotatable cutting tip 510c facing opposite apex 552c of bend 512c as well as distal tip 518c of rotatable cutting tip 510c, thus shielding tissue positioned beneath and in front of tip section 534c.

Figure 5D:
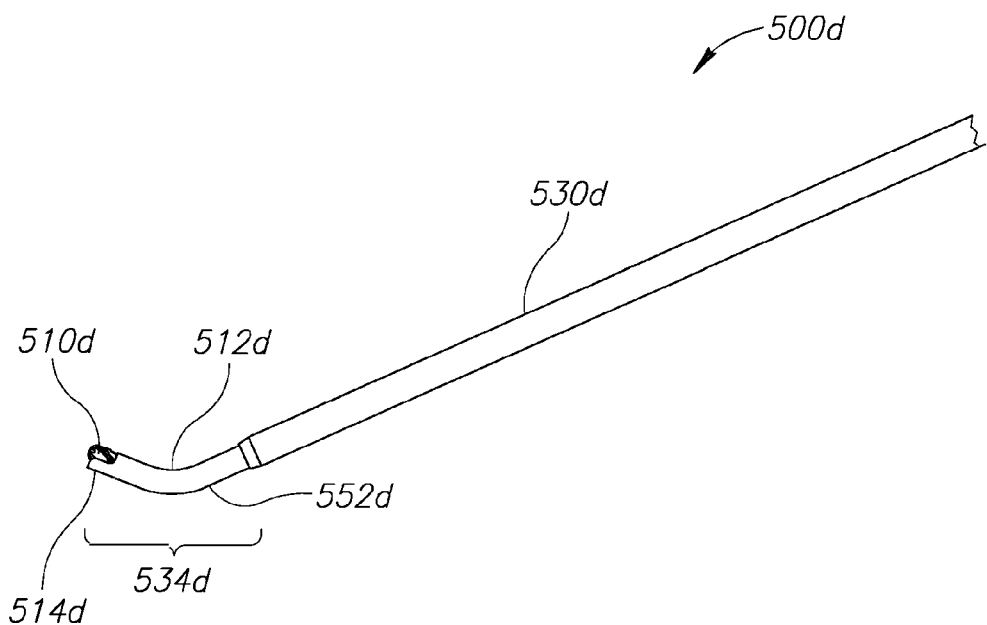
FIG. 5D is an enlarged view of a distal end of a hollow elongated member having a distal bend and a shield coextensive with the apex of the distal bend, according to some embodiments.

Reference is now made to FIG. 5D, which schematically illustrates a distal end 500d of a hollow elongated member 530d of a device for tissue removal (as disclosed herein) having a distal bend 512d. Due to distal bend 512d, tip section 534d, and thus rotatable cutting tip 510d, of hollow elongated member 530d, is offset the longitudinal axis of hollow elongated member 530d of distal end 500d, thus facilitating access to difficult to access areas, such as between and underneath vertebrae. Tip section 534d further includes a shield 514d covering a part of rotatable cutting tip 510d coextensive with apex 552d of bend 512b of rotatable cutting tip 510d, thus shielding tissue positioned beneath tip section 534d.

Figure 5E:
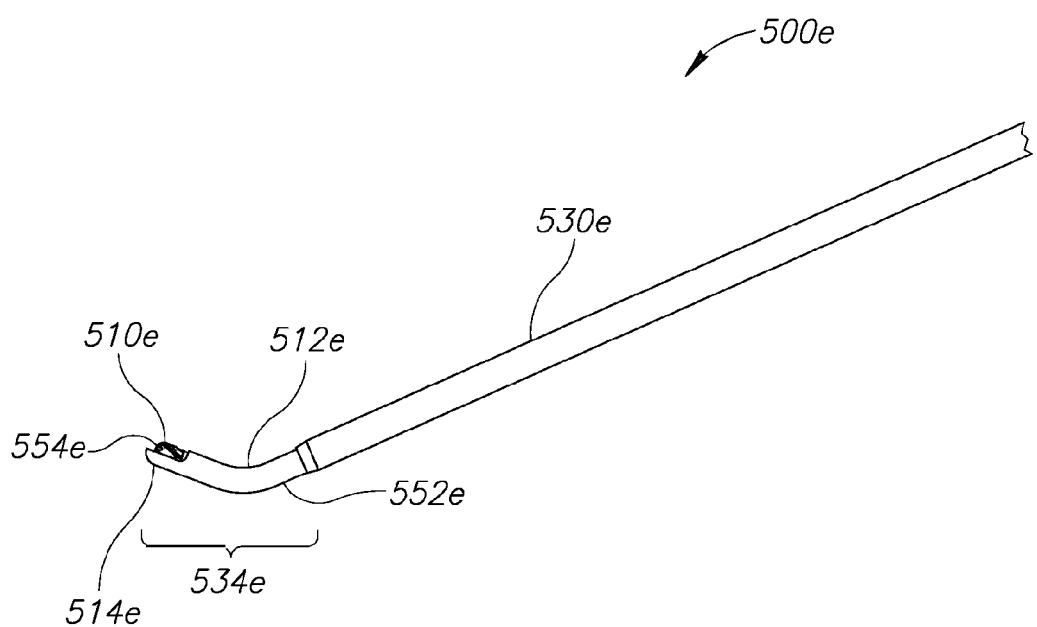
FIG. 5E is an enlarged view of a distal end of a hollow elongated member having a distal bend and a front shield coextensive with the apex of the distal bend, according to some embodiments.

Reference is now made to FIG. 5E, which schematically illustrates a distal end 500e of a hollow elongated member 530e of a device for tissue removal (as disclosed herein) having a distal bend 512e. Due to distal bend 512e, tip section 534e, and thus rotatable cutting tip 510e, of hollow elongated member 530e, is offset the longitudinal axis of hollow elongated member 530e of distal end 500e, thus facilitating access to difficult to access areas, such as between and underneath vertebrae. Tip section 534e further includes a shield 514e covering a part of rotatable cutting tip 510e coextensive with apex 552e of bend 512e as well as distal tip 518e of rotatable cutting tip 510e, thus shielding tissue positioned beneath and in front of tip section 534e.

Figure 6:
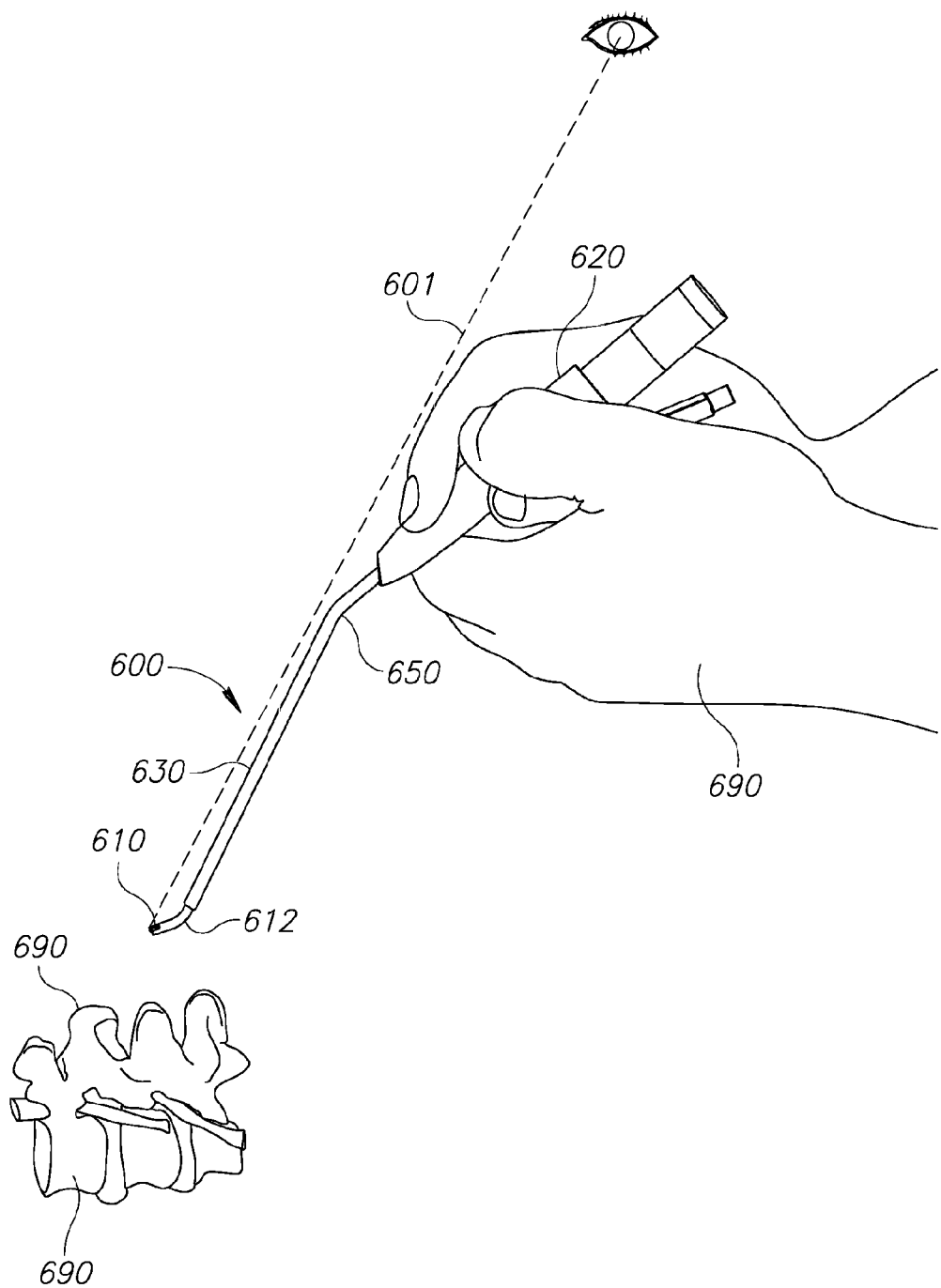
FIG. 6 schematically illustrates the device of FIG. 1A in use for interverbal disc tissue removal, according to some embodiments.

Reference is now made to FIG. 6, which schematically illustrates a device for tissue removal (such as device 100 of FIG. 1A) in use for interverbal disc tissue removal, according to some embodiments. As seen the figure, when in the hands 690 of a surgeon, proximal bend 650 of hollow elongated member 630 ensures that handle 620 does not interfere with the surgeon's line of site 601 towards rotatable cutting tip 610. In addition, distal bend 612 enables access to areas between and underneath vertebra 690 of vertebrae, thus enabling removal of tissue from areas, which are difficult to access without distal bend 612. Advantageously, the unique torque transferring assembly disclosed herein, (such as torque transferring assembly 140 or 240, not shown here) facilitate high speed torque delivery to rotatable cutting tip 610, despite bends 650 and 612.

Figure 7A:
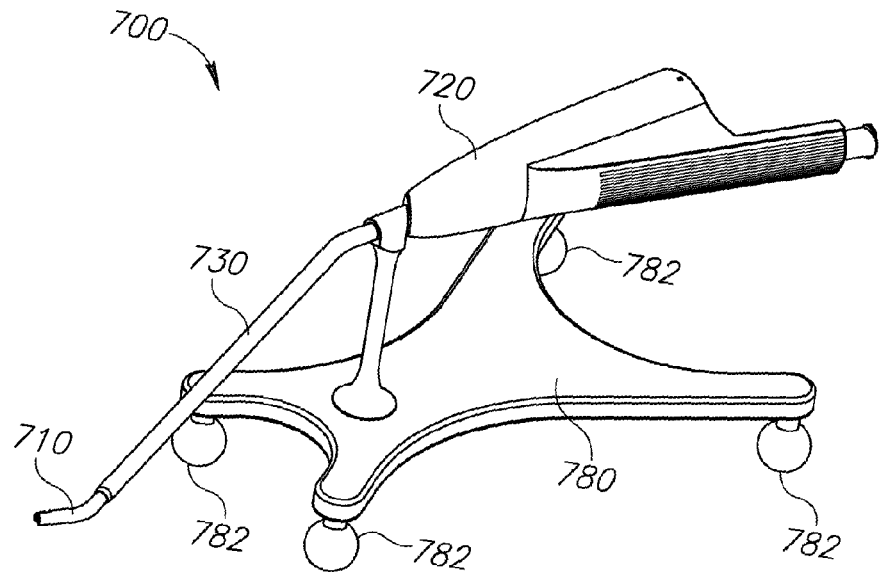
FIG. 7A schematically illustrates a front-perspective view of the device of FIG. 1A connected to an imaging plate with navigation elements, according to some embodiments.
Figure 7B:
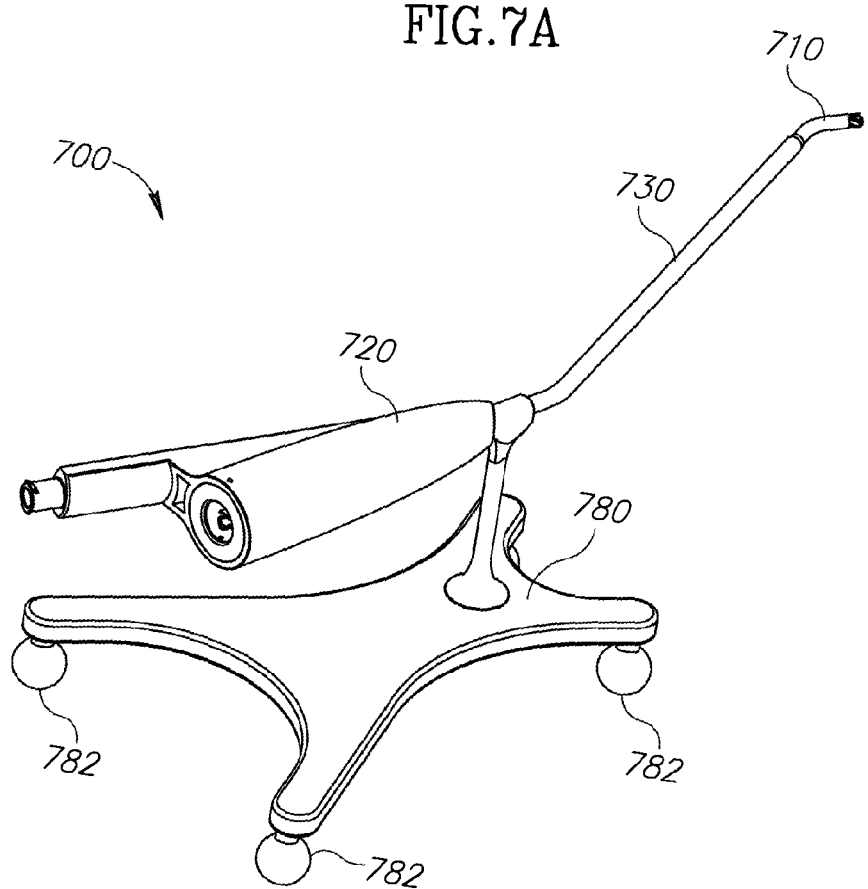
FIG. 7B schematically illustrates a back-perspective view of the device of FIG. 1A connected to an imaging plate with navigation elements, according to some embodiments.

Reference is now made to FIG. 7A and FIG. 7B which schematically illustrates a device 700 for tissue removal connected to an imaging plate comprising one or more (here 4) navigation elements 782, configured to allow determining the spatial orientation and/or coordinates of device 700, when in use. According to some embodiments, navigation elements 782 may be made of a material allowing their visualization using different visualization techniques.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising," when used m this specification, specify the presence of stated features, integers, steps, operations, elements, or components, but do not preclude or rule out the presence or addition of one or more other features, integers, steps, operations, elements, components, or groups thereof.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

The invention claimed is:

1. A surgical bone cutting system, comprising:
a surgical device comprising:
an elongated hollow member extending from said handle, said hollow member comprising a proximal end and a distal end;
wherein the hollow member comprises an opening at said distal end thereof, a torque transferring element/assembly, configured to be placed within the elongated hollow member, and a rotatable cutting element attached to said torque transferring element/assembly and extending through or positioned at said opening, and
wherein said hollow member comprises a bend at a proximal end thereof, configured to ensure that part of the hollow member distal to the proximal bend is offset a central axis of said handle, thereby ensuring visibility of said rotatable cutting element;
wherein said torque transferring element/assembly comprises a core and at least one coiled outer layer wound around the core, the core comprising a bendable multi-stranded wire, which is braided, or twisted, or interlaced or coiled and is configured to affect rotary motion of the rotatable cutting element; and
an imaging plate comprising one or more navigation elements, configured to allow determining the spatial orientation and/or coordinates of the surgical device, when in use;
wherein the torque transferring assembly further comprises a support structure configured to prevent helixing of the torque transferring assembly; and
wherein the support structure comprises one or more rigid elements configured to define rigid and bendable sections along the torque transferring assembly/element.

2. The surgical system of claim 1, wherein the one or more navigation elements is made of a material allowing optical tracking.

3. The surgical system of claim 1, wherein the one or more navigation elements comprise a spherical element.

4. The surgical system of claim 1, wherein the spherical element comprise retro-reflective balls.

5. The surgical system of claim 1, wherein the proximal bend has a bending angle of 20-60 degrees relative to the part of the elongated hollow member proximal to the proximal bend.

6. The surgical system of claim 1, wherein the first proximal bend has a bending radius of less than 20 mm.

7. The surgical system of claim 1, wherein the hollow member further comprises a bend at a distal end thereof, wherein a distance between the distal bend and the opening is less than 20 mm.

8. The surgical system of claim 7, wherein the distal bend has a bending angle of 0-60 degrees relative to part of the hollow member distal to the proximal bend.

9. The surgical system of claim 8, wherein the distal bend has a bending radius of less than 10 mm relative to part of the hollow member distal to the proximal bend.

10. The surgical system of claim 1, wherein the surgical device is a surgical drill.

11. A surgical bone cutting system, comprising:
a surgical device comprising:
an elongated hollow member extending from said handle, said hollow member comprising a proximal end and a distal end;
wherein the hollow member comprises an opening at said distal end thereof, a torque transferring element/assembly, configured to be placed within the elongated hollow member, and a rotatable cutting element attached to said torque transferring element/assembly and extending through or positioned at said opening, and
wherein said hollow member comprises a bend at a proximal end thereof, configured to ensure that part of the hollow member distal to the proximal bend is offset a central axis of said handle, thereby ensuring visibility of said rotatable cutting element;
wherein said torque transferring element/assembly comprises a core and at least one coiled outer layer wound around the core, the core comprising a bendable multi-stranded wire, which is braided, or twisted, or interlaced or coiled and is configured to affect rotary motion of the rotatable cutting element; and
an imaging plate comprising one or more navigation elements, configured to allow determining the spatial orientation and/or coordinates of the surgical device, when in use;
wherein the torque transferring assembly further comprises a support structure configured to prevent helixing of the torque transferring assembly; and wherein said support structure comprises one or more tubular elements crimped over spaced apart sections of said torque transferring elongated member coaligned with non-bend portions of said hollow elongated member.

12. A surgical bone cutting system, comprising:

a surgical device comprising:

an elongated hollow member extending from said handle, said hollow member comprising a proximal end and a distal end;

wherein the hollow member comprises an opening at said distal end thereof, a torque transferring element/assembly, configured to be placed within the elongated hollow member, and a rotatable cutting element attached to said torque transferring element/assembly and extending through or positioned at said opening, and wherein said hollow member comprises a bend at a proximal end thereof, configured to ensure that part of the hollow member distal to the proximal bend is offset a central axis of said handle, thereby ensuring visibility of said rotatable cutting element;

wherein said torque transferring element/assembly comprises a core and at least one coiled outer layer wound around the core, the core comprising a bendable multi-stranded wire, which is braided, or twisted, or interlaced or coiled and is configured to affect rotary motion of the rotatable cutting element; and an imaging plate comprising one or more navigation elements, configured to allow determining the spatial orientation and/or coordinates of the surgical device, when in use;

wherein the torque transferring assembly further comprises a support structure configured to prevent helixing of the torque transferring assembly; and wherein said support structure comprises one or more bearings positioned along a part of the torque transferring elongated member located at bend portions of said hollow elongated member.

\* \* \* \* \*